United States Patent [19]
Suh

[11] Patent Number: 5,865,623
[45] Date of Patent: Feb. 2, 1999

[54] FLEXIBLE DENTAL COMPOSITE COMPOSITIONS AND RESTORATIVE METHODS USING FLEXIBLE DENTAL COMPOSITIONS

[75] Inventor: Byoung I. Suh, Oak Brook, Ill.

[73] Assignee: Bisco, Inc., Itasca, Ill.

[21] Appl. No.: 815,794

[22] Filed: Mar. 12, 1997

[51] Int. Cl.$^6$ ...................................................... A61C 5/00
[52] U.S. Cl. ........................................................ 433/228.1
[58] Field of Search ......................... 433/228.1; 523/115; 260/998.11

[56] References Cited

U.S. PATENT DOCUMENTS

| | | | |
|---|---|---|---|
| 4,220,582 | 9/1980 | Orlowski et al. | 433/228.1 |
| 4,437,836 | 3/1984 | Schmitz-Josten et al. | 433/199 |
| 4,439,380 | 3/1984 | Michl et al. | 264/16 |
| 4,536,523 | 8/1985 | Antonucci | 433/228.1 |
| 4,816,495 | 3/1989 | Blackwell et al. | 522/14 |
| 5,037,638 | 8/1991 | Hamer et al. | 424/52 |

OTHER PUBLICATIONS

Kemp–Scholte et al., "Marginal integrity related to bond strength and strain capacity of composite resin restorative systems," *The Journal of Prosthetic Dentistry*, vol. 64, No. 6, pp. 658–664, (Dec. 1990).

Bausch et al., "Clinical significance of polymerization shrinkage of composite resins", *J. Prosthetic Dentistry* 48(*1*): 59–67 (Jul., 1982).

Davidson, "Resisting the Curing Contraction with Adhesive Composites", *J.Prosth.Dent.* 55(*4*): 446–447 (Apr. 1986).

Davidson et al., "Relaxation of Polymerization Contraction Stresses by Flow in Dental Composites", *J.Dent.Res.* 63(*2*): 146–148 (Feb., 1984).

Davidson et al. The Competition between the Composite–Dentin Bond Strength and the Polymerization Contraction Stress, *J.Dent.Res.* 63(*12*): 1396–1399 (Dec. 1984).

Feilzer et al., "Setting Stress in Composite Resins in Relation to Configuration of the Restoration", *J.Dent.Res.* 66(*11*): 1636–1639 (Nov. 1987).

Kemp–Scholte et al., "Marginal Sealing of Curing Contraction Gaps in Class V Composite Resin Restorations", *J.Dent.Res.* 67(*5*): 841–845 (May, 1988).

Kemp–Scholte et al., "Complete Marginal Seal of Class V Resin Composite Restorations Effected by Increased Flexibility", *J.Dent.Res.* 69(*6*); 1240–1243 (Jun. 1990).

"Clinical Status Praesens of Dentine Adhesives," pp. 113–115.

*Primary Examiner*—John J. Wilson
*Attorney, Agent, or Firm*—Marshall, O'Toole, Gerstein, Murray & Borun

[57] ABSTRACT

Flexible dental composite compositions and restorative compositions are provided comprising (a) about 2 to 15 weight percent of a flexible monomer portion comprising one or more flexible comonomers of the general formula $R^1-O-[(CH-R^2)_n-O-]_z-R^3$ wherein $R^1$ and $R^3$ are acrylate or methacrylate functional groups, $R^2$ is selected from the group of hydrogen, methyl and ethyl, n is from 3 to 5 and z is from about 3 to about 20 and the monomers have average molecular weights from at least about 300 or higher, (b) about 30 to about 80 weight percent of a filler portion, (c) about 18 to 60 weight percent of a comonomer portion comprising one or more comonomers capable of polymerizing with the flexible monomer portion, and (d) a polymerization catalyst system for polymerizing and hardening the composition. Compositions according to the invention are useful in Class V and other types of dental restorations. Methods for using such compositions in such restorative procedures are also provided.

23 Claims, No Drawings

FLEXIBLE DENTAL COMPOSITE COMPOSITIONS AND RESTORATIVE METHODS USING FLEXIBLE DENTAL COMPOSITIONS

FIELD OF THE INVENTION

The present invention relates generally to dental compositions and methods, and more particularly to dental restorative compositions and restorative methods using such compositions.

BACKGROUND TO THE INVENTION

Modern dental restorative procedures have recently gravitated toward the use of polymerizable resin compositions in place of metal amalgams and other traditional dental fillers. For example, in filling cavities or other defects in the tooth's surface, many dental professionals now use polymerizable resin compositions containing inorganic glass fillers to impart desired compressive strength in place of metal amalgams. Such filled polymerizable materials are easy to apply, can be colored and shaped to correspond to the original tooth surface, and often exhibit chemical adhesion to the tooth surface when polymerized as opposed to the metallic appearance and mechanical adhesion of metal amalgams.

Although filled polymerizable composite resin compositions are in widespread use, certain problems are recognized to exist due to the nature of the compositions. For example, because such composites typically depend on polymerization reactions to effect hardening of the resin in place on the tooth surface, they exert stresses on the adjacent tooth structure due to shrinkage which occurs during polymerization as the monomers move from their free liquid state into their more dense, cross-linked polymerized state. Such shrinkage and resultant stresses are often considerable, particularly in a so-called "Class V" type restoration, wherein the restoration is being effected at the dentin-enamel junction at the cervical region of the tooth, and also in so-called "Class I" restorations such as deep cavities involving restorations contacting opposing walls of the tooth. See e.g., Feilzer et al., "Setting Stress in Composite Resins in Relation to Configuration of the Restoration", *J. Dent. Res.* 66(11): 1636–1639 (November, 1987) and Davidson et al. "The Competition between the Composite-Dentin Bond Strength and the Polymerization Contraction Stress, *J. Dent. Res.* 63(12): 1396–1399 (December 1984), the disclosures of which are hereby incorporated by reference. Such shrinkage and related stresses have been reported as causing separation of the restoration from at least the dentin surface of the tooth, leading to the creation of marginal gaps between the restorative and the adjacent tooth surface. Id. See also, Bausch et al., "Clinical significance of polymerization shrinkage of composite resins", *J. PROSTHETIC DENTISTRY* 48(1): 59–67 (July, 1982), the disclosure of which is hereby incorporated by reference.

In response to these problems, much effort has focused on creation of compositions and methods to reduce or eliminate shrinkage-related stresses and marginal gaps in dental restorations. Reported approaches have included reliance on the "flow" of the composite during chemical self-curing, which proceeds slowly, (See, Davidson et al., "The Relaxation of Polymerization Stresses by Flow in Dental Composites", *J. Dent. Res.* 63(2): 146–148 (February, 1984)) or by incremental insertion of the composite in the restorative site (See Davidson, "Resisting the Curing Contraction with Adhesive Composites", *J. Prosth. Dent.* 55(1): 446–447 (April 1986.) The first "flow" study did not, however, investigate composite-dentin bonding and whether "flow" would obviate gap creation, and the incremental insertion approach was disapproved as ineffective in the next reported publication by one of the same authors. Flow dissipation of shrinkage is also believed to be limited to self-cure chemical polymerization, which occurs over a period of at least several minutes, as opposed to light or heat induced polymerization, which is often completed in a matter of 1–2 minutes or less.

Others have proposed multi-step application procedures using low-viscosity, unfilled resins to seal the marginal gaps directly after initial curing of the composite, (See, Kemp-Scholte et al., "Marginal Sealing of Curing Contraction Gaps in Class V Composite Resin Restorations", *J. Dent. Res.* 67(5): 841–845 (May, 1988)), or use of so-called "flexible" intermediate layers of unfilled resins or light-cured glass ionomer layers applied as a thin liner layer between the tooth surface and the composite. See, Kemp-Scholte et al., "Complete Marginal Seal of Class V Resin Composite Restorations Effected by Increased Flexibility", *J. Dent. Res.* 69(6) 1240–1243 (June 1990). The later study reported that the better stress release liner, the glass ionomers, actually cracked and exhibited cohesive failures. Unfilled resins are also known to exhibit significant shrinkage and generally become brittle upon curing. These multi-step, multi-material approaches also introduce complexity into the dental restoration process in terms of number of steps, materials, and increase the time spent and cost incurred by the dental professional and patient in the treatment process.

However, in addition to exhibiting good adhesion and bonding, composites and other polymerizable dental restorative material must also withstand the compressive, tensile and other forces experienced by the tooth surface in the mouth. For example, considerable compressive forces are generated by contact from other teeth during chewing and other mouth movements. The restorative may also experience tensile and abrasive forces in the mouth depending on its location on or within the tooth's surfaces. In, for example, Class V restorations, shear forces are also experienced in the restoration during mastication. Such shear forces must also be absorbed and/or dissipated or the restoration may fail. See "Clinical Status of Praesens of Dentine Adhesives" pp. 113–115, the disclosure of which is hereby incorporated by reference.

There exits, therefore, a need in the art for dental composite compositions and other restorative compositions which exhibit good bond strength, good tensile and compressive strengths; and which are easy to apply and use in dental restorative procedures.

BRIEF SUMMARY OF THE INVENTION

The present invention provides flexible dental composite compositions and restorative compositions which exhibit good bonding to tooth dentin and enamel and which also possess good tensile and compressive strengths. Such compositions include a flexible monomer portion comprising one or more flexible monomers of the general formula $R^1$—O—[(CH—$R^2$)$_n$—O—]$_z$—$R^3$ wherein $R^1$ and $R^3$ are acrylate or methacrylate functional groups, $R^2$ is selected from the group of hydrogen, methyl and ethyl, n is from about to about 5 and z is from about 3 to about 20 and the monomer or monomers have an average molecular weight from at least about 300 or higher. Presently preferred total weight amounts of the flexible monomer portion in such compositions is from about 2 to about 15 weight percent.

Also included in the compositions are a filler portion comprising one or more suitable filler materials, such as barium or other glasses, in-amounts which total from about 30 to about 80 weight percent of the composition, and a comonomer portion comprising one or more suitable comonomers in weight amounts which total about 18 to about 60 weight percent of the composition. Preferably the comonomers are capable of undergoing polymerization reactions with the flexible monomer portion. Also included in the compositions are suitable polymerization catalyst systems or compositions, such as chemical self-cure initiators, light-activated initiators and/or heat-activated polymerization initiators.

The present invention also contemplates dental restorative methods wherein flexible compositions of the present invention are used as composite restorative materials. In addition, dental restorative methods are contemplated wherein flexible compositions of the present invention are applied as liners in restoration sites and accept conventional, inflexible composite restorative compositions.

DETAILED DESCRIPTION OF THE INVENTION

The compositions of the present invention and methods for their use have particular application in the field or restorative dentistry. The compositions according to the present invention comprise a flexible monomer portion, a filler portion, a comonomer portion and a polymerization catalyst portion comprising a polymerization compound or system. Optionally, the compositions may include antimicrobial agents, opaquifiers, fluoride-release agents, colorants and other components which impart desirable properties to the composition. Such additional agents may be incorporated into one or more of the flexible monomer, comonomer or finer portions of the compositions, or may be added in small amounts to the composition during formulation.

Flexible monomers which may be used in the composition and methods of the present invention have the general formula:

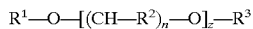

$$R^1-O-[(CH-R^2)_n-O]_z-R^3$$

wherein $R^1$ and $R^3$ are acrylate or methacrylate functional groups. Preferably, $R^1$ and $R^3$ are the same. $R^2$ is either hydrogen (H), methyl or ethyl. The flexible monomers have an average molecular weight of at least about 300, preferably from about 400 to about 2000, and more preferably about 400 to about 1200, with n being from about 3 to about 5 and z being from about 3 to about 20. Dimethacylates of polypropylene glycol (PPGDMA) or polytetramethlyene glycol (PTMGDMA) are presently preferred flexible monomers according to the invention. The presently preferred flexible monomers of the invention may be manufactured in the laboratory by well-known methods or may be purchased from commercial sources such as PPGDMA and PTMGDMA from Monomer-Polymer and Dajac Laboratories, Inc. in Trevose, Pa. Such commercial monomers are available in average molecular weights of from about 200 to about 4000. Those of ordinary skill in the art will recognize that higher molecular weight monomers of about 1200 or higher may require dissolution in a suitable diluent monomer before formulation in composition according to the present invention. At present, monomers having an average molecular weight of less than 2000, i.e. from about 400 to about 1200 are more preferred in the present invention for reasons such as ease of formulation. PTMGDMA having an average molecular weight of about 600 is presently a preferred monomer.

Presently preferred amounts of flexible monomer(s) in compositions of the present invention are from about 2 to about 15 weight percent of the total composition. Presently more preferred amounts are in the range of about 5 to about 10 weight percent of the composition. It is also contemplated that the flexible monomer portion within these ranges may include two or more flexible monomers of the above-described general formula.

Fillers according to the present invention may include one or more well-known metal oxides and glasses. For example, finely divided fillers are silanated oxides of aluminum, zirconium and silicon, silicate glasses, and barium or strontium glasses. Preferred contemplated filler particles have an average size of about 0.02 to about 20 microns. Presently more preferred fillers have an average particle size of about 0.04 to about 5 microns. Presently more preferred fillers are of a micron or submicron average particle size of about 0.7 to about 1 micron. The use of sub-micron size fillers in the compositions of the present invention is presently preferred to minimize surface wear and "plucking" of filler components from the restorative surface, as well as imparting a surface which may be easily polished by the dental professional. Also, handling characteristics such as bulk and consistency are improved. Flow and/or slump are minimized for better restoration placement in cavity preparations.

One or more of the aforementioned fillers comprising the filler portion may also include caries inhibiting agents such as slow releasing fluoride agents to help inhibit caries from forming in the adjacent tooth structure. For example, glass ionomer 1X 1944 from Ferro Corporation, Cleveland, Ohio, which contains such a slow release fluoride agent, is expected to have utility in the present invention.

The filler or fillers are present at about 30 to about 80 weight percent of a contemplated compositions of the present invention, and are more preferably present at about 40 to about 60 weight percent of the composition. The amount of the filler component is adjusted in view of the other components of the composition and in view of the intended use of the composition, it being well-known in the art that higher filler amounts generally impart higher compressive strengths to a composition, but also tend to increase viscosity and decrease flowability of the composition. Presently preferred fillers include silanized barium glass from Ferro Corporation, Cleveland, Ohio, and silanized submicron glasses such as OX-50 or Aerosil R972 from DeGussa, Richfield Park, N.J.

Preferably, the filler portion is formulated to include appropriate coloring agents in varying amounts to provide the dental professional with a range of colors in the composition which may be selected for compatibility with the shade of the patient's tooth undergoing restoration. Such coloring or tint agents are well-known in the art, and may be included in small amount of about 1 weight percent or less of the total composition. Such fillers can also be selected to be radiopaque. For example, appropriate amounts of radiopaque barium, strontium or zirconium glass may be used as all or part of the filler portion, which can assist the dental professional in his or her post-treatment examination of the patient.

The compositions of the present invention also include suitable comonomer(s) containing one or more functional groups capable of polymerization reaction with one or more of the flexible monomers in the flexible monomer portion of the composition, and more preferably capable of polymerizing with each type of flexible monomer in the flexible monomer portion. Such comonomer(s) are preferably present in amount of from about 18 to about 60 weight percent of the composition. The amount of the comonomer portion in the overall composition is dependent in part on the amount of filler and elastic monomer in the composition and in part on the desired viscosity and flow characteristics of the composition, it being recognized that the comonomer(s) may also be selected to act as diluents to assist in formulating the compositions.

Suitable comonomers may include well-known mono-, di-, tri- and tetraacrylate and methacrylates such as 2,2-bis [4-(3-methacryloxy-2-hydroxypropoxy)phenyl]-propane (BISGMA), Bisphenol A dimethacrylate (Bis A Dima), ethoxylated Bis A Dima, neopetylglycol dimethacrylate, decanediol-1,10-dimethacrylate, dodecanediol-1,12-dimethacrylate, 1,4-butanediol dimethacrylate, ethyleneglycol dimethacrylate, diethyleneglycol dimethacrylate, triethyleneglycol dimethacrylate (3 EGDMA), tetraethyleneglycol dimethacrylate (4 EGDMA), polyethyleneglycol dimethacrylate, propyleneglycol dimethacrylate, dipropyleneglycol dimethacrylate, tripropyleneglycol dimethacrylate, tetrapropyleneglycol dimethacrylate, polypropyleneglycol dimethacrylate, hexamethyleneglycol dimethacrylate (HMDA), 2,2-bis(4-methacryloxyphenyl) propane, 2,2-bis(4-methacryloxyethoxyphenyl)propane, 1,2-bis(3-methacryloxy-2-hydroxypropoxy)ethane, CPDM the reaction product of cyclopentane tetracarboxylic acid dianhydride and 2 moles of hydroxyethyl methacrylate (HEMA), tetrahydrofurfuryl cyclohexene dimethacrylate (TCDM) the reaction product of Epiclon B-4400 (Dainippon Inc. and Chemicals Inc., Ft. Lee, New Hersey) with 2 moles of HEMA, 2,2-bis(4-methacryloxyphenyl)propane, 2-hydroxy-1,3-dimethacryloxypropane, di-2-methacryloxyethyl-2,2,4-trimethylhexamethylene dicarbamate (UDMA), di-2-methacryloxyethylisophorone dicarbamate, and di-2-methacryloxyethyl-2,4- or 2,6-tolylene dicarbamate. Of the above monomers, the use of BISGMA and/or UDMA and 3 EGDMA are presently preferred. It is presently preferred that the comonomer(s) be selected such that they contain two functional groups which are capable of undergoing polymerization reactions with the flexible monomer(s) to help impart good flexure and tensile strength to the composition as well as a relatively high degree of cross-linking throughout the composition.

Presently preferred comonomer portions include the admixture of two or more of such comonomers. For example, Bis-GMA and 3 TEGDMA in a ratio of from about 1:1 to about 4:1 have been found to have utility in the present invention.

Optionally, one or more of the comonomer compounds may include a caries inhibiting agent that helps to prevent or inhibit caries formation in the adjacent tooth structure. For example, the fluoride release monomer disclosed in U.S. Pat. No. 5,037,638, whose disclosure is incorporated by reference, may have utility in the present invention as part of the comonomer portion of the composition.

A polymerization catalyst compound, composition or system is also included in the contemplated composition of the present invention. Such polymerization compounds, compositions or systems (hereinafter referred to as "systems") are well known in the art. They generally fall within one of three categories: (1) self-curing chemical systems which initiate polymerization upon admixing two or more compounds; (2) light-initiated polymerization systems; and (3) heat-initiated polymerization systems. A polymerization system employing two or more initiators, i.e. light/self cure or light/heat initiated systems is also contemplated to give the dental professional additional flexibility in the restorative procedures.

Exemplary self-curing systems include traditional free radical polymerization initiators normally used with polymerizable ethylenically unsaturated materials and resins. For example, organic peroxide initiators and amine accelerations such as those disclosed in U.S. Pat. No. 4,816,495, whose disclosure is hereby incorporated by reference, may be used, and, as taught therein, packaged separately from the polymerizable monomer components of the system and admixed with the monomers shortly before application to the tooth or dental appliance.

A light or photo-curing or photosensitive polymerization initiation and curing system is also included in a contemplated light-curable flexible composition of the present invention. A contemplated photo-curing system is activated to harden and cure the composition by irradiation with visible or UV light. For example, visible light of a wavelength of about 400 to about 500 $\mu$m initiates rapid and efficient curing.

Such systems are well-known and typically include a light or photoinitiator that is usually benzophenone or a derivative, or an $\alpha$-diketone such as benzil or camphorquinone; camphorquinone being presently preferred. Also included is tertiary amine reductant or its salts. Exemplary tertiary amines include tributylamine, tripropylamine, N-alkyldiaLktnol amines such as N-methyldiethanolamine, N-propyldiethanolamine, N-ethyldiisopropanolamine and trialkandamines' such as triethanolamine and triisopropanolamine. Further useful tertiary amines are specifically disclosed in U.S. Pat. No. 4,439,380 and No. 4,437,836 and 4,816,495. Ethyl 4-dimethylamino benzoate (EDMAB) is a presently preferred tertiary amine reductant.

The photo-curing system is present in an amount sufficient to cure the cement to a desired strength within about two minutes upon irradiation with light as above. More preferably, the cure time is less than about one minute, and most preferably about 20 to about 30 seconds. In usual practice, both components of the photo-curing system constitute less than about two percent of the weight of the flexible dental compositions of the present invention, and more preferably less than about 1 weight percent.

Heat-initiated polymerization systems are also contemplated in the compositions of the present invention. Preferred heat initiators are those which initiate curing at around 60 to 150 degrees Centigrade, and more preferably about 100 to 130 degrees Centigrade. Such systems include benzoyl peroxide, t-butyl perbenzoate, 1,1,-di(tert-butyl) peroxide and other well-known catalysts capable of initiating polymerization of ethylenically unsaturated groups or resins.

Still further ingredients such as pigments, tints, stabilizers, surfactants, fluoride release agents and thickening agents may be added to the composition to enhance its stability, color and beneficial properties. For example, well-known UV absorbers such as Uvinul® 3000 available from BASF Corp. can be present at less than about 0.5 weight percent, and polymerization inhibitors such as hydroquinone monomethyl ether (MEHQ) or 2,6-di-tert-butyl-4-methylphenol (BHT) that can be present at less than 0.1 weight percent, and more usually at less than 0.01 weight percent in the composition. MEHQ is preferred as the polymerization inhibitor.

As indicated above, it is also contemplated that the polymerization initiator system of the present invention may include two or more initiators in the composition. For example, a combination of a light cure initiator system utilizing CQ alone or in combination with a tertiary amine reductant along with a heat curing agent such as t-butyl perbenzoate is expected to have utility in the present invention. Such multi-initiator systems may have utility in that they may include both a rapid cure initiator (light or heat cure) to impart significant polymerization in the dental office or dental laboratory. For example, a light cure systems in combination with a longer time self-cure initiator which continues to cause further polymerization after the patient leaves the office and further secures the restorative to the tooth structure is also contemplated.

Such dual cure light/heat systems, as well as their respective single initiator systems, are also desirable in that they may be formulated and packages in one container or syringe, thereby avoiding the need for mixing by the dental professional before application. For example, as set out in the following examples, such one-component systems exhibit good shelf life of more than a year when stored away from light at room temperature. If self-curing compositions are desired, the self-curing initiator may be packaged in one of two containers separately from the polymerizable components of the composition, with the contents of both containers being admixed shortly before use in the dental office.

Preferred methods of use of the aforementioned compositions include their use as composite in classic dental restorative procedures such as Class V restorations. Such methods include the usual cleaning and preparation of the tooth surface, followed optionally and preferably by application of a dental adhesive composition, followed by application and curing of the flexible dental compositions indicated above. For example, prepared restorative sites may be pre-treated with dental bonding adhesive systems such as "One Step" or "ALL BOND 2" from Bisco, Inc., Itasca, Ill. according to the manufacturer's instructions. Compositions according to the present invention are then applied to the tooth, preferably by syringe in incremental layers of about 0.5 to about 2 mm and cured for about 20–40 seconds (depending on the shade of the composition, darker having higher application times), followed by additional layers and curing until the cavity is completely filled to the cavosurface margin. Any excess material is removed immediately from the surface and the restoration is finished and polished by conventional techniques such as diamonds, discs and polishing pastes. Such finishing also removes any oxygen-inhibited uncured or partially cured layer on the surface of the restoration which if left in place might cause staining of the surface over time.

It will also be appreciated by those skilled in the art that the flexible dental compositions and the methods of the present invention have significant utility in other restorative applications.

For example, compositions of the invention may also be used as liners in Class I, II or III restorations. In Class I and II restorations, which typically experience considerable occlusal forces from mastication, use of conventional inflexible, highly filled and hard composites has often lead to problems such as creation of marginal gaps. Use of the flexible compositions according to the present invention as liners under such conventional compositions permits their use and avoids such gaps.

Other areas of use of the present inventions which will occur to those of skill in the art include without limitation: use of the compositions under temporary crowns, so-called Class III type restorations, small non-stress Class IV repairs, porcelain veneer bonding, tunnel preparation, splinting, marginal defect repair, deciduous class I or II repair, impart seals, buccal pit restorations, porcelain repair, pit and fissure sealant, adult preventative resin and small core build-up applications.

The following examples are given by way of illustration but without limitation. All parts and percentages are by weight unless otherwise noted.

EXAMPLE 1

Flexible dental compositions were formulated according to the following procedures.

A. 3 EGDMA Diluent Monomer/Photoinitiator. A diluent monomer solution containing a polymerization initiator system and other compounds was formulated by admixing 83.15% 3 EGDMA from Esschem Company, Essington, Pa., with 0.05% MEHQ from Aldrich Chemical Company, Milwaukee, Wis., 5.00% Uvinol-3000 from BASF Corporation, Mount Olive, N.J., 8.00% Bisphenol A Dima from Hampford Research, Inc., Stratford, Conn., 3.00% EDMAB from Aldrich Chemical and 0.80% CQ from Hampford Research, Inc. The mixture was protected from light during and after such mixing.

B. Resin Solution. The aforementioned diluent monomer solution and photoinitiator system was combined with ethoxylated Bisphenol A Dima and PTMGDMA in the following amounts: 55.0% ethoxylated Bisphenol A Dima, 15.00% PTMGDMA (#9662, average m.w. 600 from Monomer-Polymer and Dajac Laboratories, Inc., Trevose, Pa.) and 30.0% 3 TEGDMA solution. The mixture was also protected from light during and after this formulation step.

C. Tinted Fillers. A series of ten tinted fillers of varying standard Vita shades of color (A1, A2, A3.5, C2, D3, A20, A3, B3, C3, A5) were prepared by admixing from 89.027 to 91.530% silanized barium glass (Schott, Germany) with varying amount of well-known coloring agents and small amounts of TiO2.

D. Composition formulation. A series of ten flexible dental compositions were prepared by admixing resin solution B with each of the tinted fillers identified in section C above in the following amounts: 40.0% resin and 60.0% tinted filler. Each admixture was protected from light during admixture, and were placed in separate, light-opaque syringes immediately after mixture.

The resultant compositions exhibited good viscosity and flowability, and were easily dispensable from their syringes. In terms of total weight of the composition, the compositions included about 6% PTMGDMA, about 12% 3 EGDMA and about 55% filler.

EXAMPLE 2

One of the compositions of Example 1, comprising 55.074% filler, 6% PTMGDMA and about 10% 3 EDGMA was tested for its tensile strength (DTS), compressive strength (CS), Barcol Hardness (935), flexural modulus (FM), and water sorption according to the following methods.

A. Sample Preparation. A diametral tensile strength (DTS) test specimen of the above-identified composition was prepared by filling a 6 mm diameter and 3 mm deep stainless steel cavity mold. The composition was light-cured for 40 seconds on each side (2×40 sec.) using a 500 milliwatt light source such as an Optilux 400, Demetron Research Corp., Dansbury, Conn.) light source.

A Compressive Strength (CS) specimen of the same composition was prepared in a similar manner by filling a 4 mm diameter by 6 mm deep two-piece stainless steel mold followed by light curing on each side for 60 seconds (2×60 sec.) using the light powered source and intensity indicated for the DTS specimen.

Flexure strength and flexure modulus of the composition were determined by creating bar-shaped specimen (25 mm×2 mm×2 mm) from a two-piece stainless steel mold. Curing was effected using the same light source and intensity indicated above but applied for 2×40 sec. on one side of the mold.

B. Strength and Flexibility Testing

Diametral tensile strength, compressive strength, flexure strength and flexure modulus were measured by loading each specimen to failure on a Model 4466, Instron Corp., Canton, Mass. for DTS and CS tests and on a QTest 4, MTS Systems, Cary, N.C. for the FS and FM tests. Eight to ten specimens were broken for each test, and the results averaged. A cross-head speed of 10 mm/min. was used for compression strength and diametral tensile strength testing, while a cross-head speed of 0.75 mm/mn. was used for flexure testing.

C. Results. The foregoing testing yielded the following results:

| Test | Results (ave.) |
| --- | --- |
| DTS | 42 Mpa |
| CS | 288 Mpa |
| Barcol Hardness | 89 (top) |
|  | 82 (bottom) |
| Flexural Modulus |  |
| Immediate | 1.051 GPa +/− .158 |
| 24 Hours | 3.608 GPa +/− .541 |

Flexure modulus values were measured immediately after curing on one set of samples, and after curing and subsequent immersion in water at 37 degrees Centigrade for 24 hours.

4. Water sorption. Water sorption of the composition was also determined according to ANSI/ADA Specification No. 27 (1993) for resin based filler materials. The cured sample exhibited a water sorption of 8.33 ug/mm3.

The above values demonstrate that the composition exhibited good flexibility, tensile strengths and Barcol hardness. Very low modulus of flexibility were observed for the composition, i.e. only about 1.05 GPa immediately after curing, and only about 3.6 GPa after 24 hours immersion in water at physiological temperature. Such values are well below those for conventional filled composites. Those low modulus values for the composition, considered along with its good flexibility and tensile strength and water sorption, indicate that the composition is well suited as a restorative material in Class V restorations and other applications involving shear and tensile stresses, and can dissipate those as well as internal shrinkage-induced polymerization stresses.

EXAMPLE 3

The effect of varying the amounts of a flexible monomer component in compositions of the present invention was investigated according to the following procedure.

Sample Preparation. Three dental composition were prepared using 0, 10 and 20% PTMGDMA in combination with the following amounts of Bis GMA and 3 EDGMA solutions:

Sample A. 0% PTMGDMA, 50% Bis GMA, 20% 3 EDGMA and 30% EDGMA solution comprised of 97.29% 3 EDGMA, 2% EDMAB, 0.7% CQ and 0.01% MEHQ (hereinafter referred to as 3 EDGMA/initiator solution.)

Sample B. 10% PTMGDMA, 45% Bis GMA, 15% 3 EDGMA and 30% 3 EDGMA/initiator system.

Sample C. 20% PTMGDMA, 40% Bis GMA, 10% 3 EDGMA and 30% 3EDGMA/initiator solution.

Eight to ten specimens of each sample were cured and tested for flexural modulus according to the method of Example 2. In addition, each sample was tested for peak stress exhibited immediately after curing and within 24 hours using the flexure modulus method of Example 2.

B. Results. The following results were observed for the above-identified tests.

| Sample | Test | Results |
| --- | --- | --- |
| A | FM-initial | 0.85 +/− 0.06 |
|  | FM-24 hrs. | 2.10 =/− 0.06 |
| B | FM-initial | 0.70 +/− 0.06 |
|  | FM-24 hrs. | 1.69 +/− 0.04 |
| C | FM-initial | 0.59 +/− 0.09 |
|  | FM-24 hrs | 1.26 +/− 0.14 |
| A | Peak Stress-initial | 44.96 MPa +/− 3.3 |
|  | Peak Stress-24 hrs | 71.11 Mpa +/− 18.5 |
| B | Peak Stress-initial | 43.20 MPa +/− 1.94 |
|  | Peak Stress-24 hrs | 72.57 MPa +/− 7.47 |
| C | Peak Stress-initial | 39.06 MPa +/− 2.7 |
|  | Peak Stress-24 hr | 63.58 MPa +/− 2.2 |

Inclusion of the flexible monomer compound in the above resins lowered their flexure modulus. Similar relative reduced flexure modulus was observed in other unfilled resin samples wherein the PTMGDMA was the selected flexible monomer and was varied in 5% increments from 0% to about 25% of the total unfilled resin component. The 24 hour flexure modulus decreased fairly linearly from about 11.11 to about 6.76 over that range of increasing flexible monomer. As indicated above, inclusion of PTMGDMA also generally decreased stresses caused by polymerization shrinkage.

Samples A, B and C were also tested for Barcol hardness and DTS at 24 hrs according to the methods of Example 2. They yielded the following results: Sample A- initial Barcol hardness of 89 top/88 bottom, DTS (2 runs) average of 32 MPa +/−4.9; Sample B- initial Barcol hardness of 86/84, DTS (2 runs) of an average of 31 MPa +/−6.2; Sample C- initial Barcol hardness of 80/78, DTS (2 runs) of 29 MPa +/−7.3. Inclusion of small air bubbles in the unfilled resins could not be avoided, and may have contributed to lower DTS observed values.

EXAMPLE 4

The effect of varying the amount of flexible monomer in another filled composite was investigated.

Sample Preparation. The control composition, Sample 1, was comprised of about 73% filler (66.4% barium glass (Schott, Germany), 5.1% Ox-50 and 1.5.0% Aerosil R792) and about 27% resin (16.2% Bis GMA, 0.9% Bis Phenol A Dimethacrylate, 9.0% 3 EGDMA, trace of MEHQ (<0.01%), 0.5% UV-3000, 0.3% EDMAB, 0.1% CQ).

Sample 2 contained the same components in the same amounts, except that 10% PTMGDMA was substituted in place of a like amount of the Bis GMA in the resin portion of the composition. Sample 3 was also prepared, but the amount of PTMGDMA was increased to 20% in the resin portion of the composition in place of a like amount of Bis GMA. Thus, Samples 1, 2 and 3 contained 0%, 2.7% and 5.4% PTMGDMA respectively measured in terms of total weight percent of the compositions.

The effect of the aforementioned varying monomer content of a resin was investigated by evaluating a material's diametral tensile strength, compressive strength, flexure strength, flexure modulus according to the methods of Example 2. The sample's mixed mode fracture toughness was also evaluated according to the procedure outlined below.

B. Mixed Mold Fracture Toughness Test Methods. Mixed mode fracture toughness values were obtained from specimen made from a stainless steel mold (diameter 25 mm and thickness 2 mm) and cured for two minutes on each side (Triad II, Dentsply International Inc., York, Pa.) (3). A chevron notch with an initial crack length of $a_o=2$ mm was machined in the middle of each specimen using steel blades 20 mm in diameter and 0.75 mm in thickness (see FIG. 1).

Diametral tensile strength, compressive strength, flexure strength and flexure modulus were measured by loading each specimen to failure (Model 4466, Instron Corp., Canton, Mass. for DTS and CS tests and QTest 4, MTS Systems, Cary, N.C. for FS and FM tests). Thirty specimen were broken for each test: ten for each monomer composition investigated. A cross-head speed of 10 mm/min. was used for compression strength and diametral tensile strength testing, while a cross-head speed of 0.75 mm/mn. was used for flexure testing.

C. Results. The mean diametral tensile strength values, compression strength values, flexure strength and flexure modulus values are shown in Table 1. Fracture toughness values are listed in Table 2.

TABLE 1

Experimental Determination of DTS, CS, FS and FM With Varying Monomer Content

| % PTMGDMA | DTS (MPa) | CS(MPa) | FS(MPa) | FM(MPa) |
|---|---|---|---|---|
| 0.0 | 47.6 ± 7.2 | 285.8 ± 47.4 | 140.0 ± 26.1 | 14.8 ± 2.8 |
| 2.7 | 47.4 ± 4.9 | 287.3 ± 29.5 | 102.6 ± 22.5 | 12.7 ± 0.9 |
| 5.4 | 45.1 ± 4.3 | 288.4 ± 31.1 | 94.3 ± 10.8 | 8.2 ± 0.3 |

As can be seen, there is a decrease in flexure strength as the monomer content increases. Furthermore, this change also causes nearly a 45% decrease in flexure modulus. Diametral tensile strength and compressive strength, on the other hand, do not seem to be sensitive to changes in monomer content.

TABLE 2

Experimental Determination of Mode 1 and Mode II FT

| % PTMGDMA | FT [at 0° $K_{IC}$] (MPa*m$^{0.5}$) | FT [at 15° $K_{IC}$] (MPa*m$^{0.5}$) | FT [at 15° $K_{IIC}$] (MPa*m$^{0.5}$) | FT [at 29° $K_{IIC}$] (Mpa*m$^{0.5}$] |
|---|---|---|---|---|
| 0.0 | 0.946 ± 0.172 | 0.569 ± 0.007 | 0.810 ± 0.112 | 1.793 ± 0.479 |
| 2.7 | 1.117 ± 0.327 | 0.692 ± 0.276 | 0.989 ± 0.394 | 2.029 ± 0.458 |
| 5.4 | 1.203 ± 0.243 | 1.028 ± 0.123 | 1.465 ± 0.179 | 1.527 ± 0.180 |

The values in Table 2 indicate that there was not a statistically significant change in Mode I fracture toughness. At $\alpha=15°$, Mode II fracture toughness values had a tendency to increase with increasing monomer content.

Flexure strength measurements are useful in evaluating a material because they involve both tensile and compressive stresses under loading. As the load is applied along the length of the bar-shaped specimen, the side in direct contact with the applied load is subjected to compression, while the opposite parallel side is subjected to tensile forces. Since tooth restorations in the mouth undergo complex stresses, it is of interest to consider tests which are similar in nature to that which naturally occurs. The flexure strength values indicate that the composite becomes more flexible (elastic) as more monomer is added to the resin, although the flexure strength decreases. This increase in elasticity may adversely affect the flexure modulus of a material. Since an increase in elasticity may increase the deflection under a given load, the flexure modulus decreases as the monomer content is added.

To those skilled in the art to which this invention relates, other changes in construction and different embodiments and applications of the invention will suggest themselves without departing from the spirit and scope of the invention. The foregoing disclosures and the descriptions herein are illustrative and are not intended to be in any sense limiting.

What is claimed is:

1. A flexible dental composite composition comprising:
   (a) from about 2 to about 15 weight percent of a flexible monomer portion comprising one or more flexible monomers of the formula

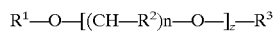

wherein $R^1$ and $R^3$ are selected from the group consisting of acrylate or methacrylate, $R^2$ is hydrogen, n is from about 3 to about 5, and z is from about 3 or higher and the average molecular weight of each of said flexible monomer is from about 300 or higher;

(b) from about 18 to about 60 weight percent of a comonomer portion comprising one or more suitable comonomers having at least one unsaturated group capable of undergoing a polymerization reaction with said flexible monomer portion;
   (c) from about 30 to about 80 weight percent of a filler portion comprising one or more suitable filler materials; and
   (d) an amount of a suitable polymerization catalyst system capable of initiating polymerization of said flexible monomer and diluent monomer and hardening of said dental composite composition after application of said composite to the tooth or dental appliance.

2. A flexible dental composite composition according to claim 1 wherein one or more of said flexible monomers is a diacrylate or dimethacrylate monomer.

3. A flexible dental composite composition according to claim 1 wherein said flexible monomer portion comprises from about 5 to about 10 weight percent of said composition.

4. A flexible dental composite composition according to claim 1 wherein said flexible monomer or monomers have an average molecular weight from about 400 to about 1200.

5. A flexible dental composite composition according to claim 1 said flexible monomer or monomers have an average molecular weight from about 400 to about 800.

6. A flexible dental composite composition according to claim 5 wherein said flexible monomer portion is comprised of PTMGDMA.

7. A flexible dental composite composition according to claim 1 wherein one or more of said flexible monomers is PTMGDMA.

8. A flexible dental composite composition according to claim 1 wherein said filler portion is from about 40 to about 60 weight percent of said composition.

9. A flexible dental composite composition according to claim 1 wherein said filler portion comprises one or more fillers selected from the group consisting of silanated aluminum oxide, zirconium oxide, silicon oxide, barium glass, strontium glass and silicate glasses.

10. A composition according to claim 9 wherein said light initiator is CQ.

11. A flexible dental composite composition according to claim 1 wherein said filler portion comprises one or more suitable fillers having an average particle size of from about 0.02 to about 20 microns.

12. A flexible dental composite composition according to claim 1 wherein said filler portion comprises one or more fillers having an average particle size of from about 0.04 to about 5 microns.

13. A composition according to claim 12 wherein said tertiary amine is EDMAB.

14. A flexible dental composite composition according to claim 1 wherein said filler portion comprises one or more fillers having an average particle size of about 0.7 to about 1 micron.

15. A flexible dental composite composition according to claim 1 wherein said comonomer portion comprises one or more comonomers selected from the group consisting of 3 EDGMA, BIS-GMA and ethoxylated Bis-A Dima.

16. A flexible dental composition according to claim 1 wherein said catalyst system includes a light initiator.

17. A flexible dental composite composition according to claim 1 wherein said catalyst system includes a tertiary amine reductant compound.

18. A flexible dental composite according to claim 1 wherein said polymerization initiator system includes a photoinitiator system and a heat-sensitive polymerization initiator system.

19. A method of restoring a tooth comprising:

(a) cleaning and preparing the surface of the tooth to be restored;

(b) applying the flexible composite composition according to claim 1 to the prepared tooth surface;

(c) causing said composition to polymerize and harden.

20. The method according to claim 19 wherein said polymerization is initiated by directing a suitable light source to the applied flexible composite composition.

21. A method of restoring a tooth comprising:

(a) cleaning and preparing the tooth surface, (b) applying a thin layer of a flexible composite composition according to claim 1 to the prepared surface, (c) causing said flexible composite to at least partially polymerize, and (d) applying a filled restorative material to said at least partial polymerized flexible composite layer and causing said applied restorative to polymerize and harden.

22. A method of restoring a tooth comprising by applying a dental appliance thereto comprising:

(a) cleaning and preparing the tooth surface, (b) applying a thin layer of a flexible composite composition according to claim 1 to the dental appliance and/or to the prepared surface, (c) applying the coated appliance to the prepared surface of the tooth, and (d) causing said composite to polymerize and harden and to affix the appliance to the tooth.

23. A flexible dental composite composition comprising from about 2 to about 10 weight percent of PTMGDMA, about 40 to about 80 weight percent of a filler portion comprising one or more suitable fillers, about 10 to about 58 weight percent of a comonomer portion comprising one or more suitable comonomers having at least one functional group capable of undergoing a polymerization reaction with PTMGDMA, and an amount of a polymerization catalyst composition or system capable of initiating said polymerization reaction and hardening said dental composite composition after said composition is applied to the tooth or dental appliance.

* * * * *